United States Patent [19]

Chernack

[11] Patent Number: 4,979,503

[45] Date of Patent: Dec. 25, 1990

[54] HAND-HELD ORAL IRRIGATING DEVICE

[75] Inventor: Milton P. Chernack, West Hempstead, N.Y.

[73] Assignee: Hydrodent Laboratories Inc., Woodbridge, N.J.

[21] Appl. No.: 444,772

[22] Filed: Dec. 1, 1989

[51] Int. Cl.⁵ .............................................. A61H 9/00
[52] U.S. Cl. ........................................ 128/66; 433/88
[58] Field of Search ...................... 128/66; 433/80, 88, 433/85

[56] References Cited

U.S. PATENT DOCUMENTS

| | | | |
|---|---|---|---|
| 3,820,532 | 6/1974 | Eberhardt et al. | 128/66 |
| 4,108,167 | 8/1978 | Hickman et al. | 128/66 |
| 4,564,005 | 1/1986 | Marchand et al. | 128/66 |

Primary Examiner—John J. Wilson
Attorney, Agent, or Firm—Cohen, Pontani & Lieberman

[57] ABSTRACT

The hand-held oral irrigating device of the invention is substantially self-contained and powered solely by an input stream of continuous flow treatment liquid, such as water from a conventional supply line. The device includes a internal turbine that is rotated by one portion of the input stream and which generates a pulsatile flow of the treatment liquid from a second portion of the stream by interruptedly passing the second portion through apertures defined in the rotating turbine. The rotating turbine concurrently operates a gear pump for mixing a stored medicament, at a rate controlled by the rotation of the turbine, with the pulsatile flow of treatment liquid at a predetermined and substantially constant volumetric ratio. The resulting combined pulsatile flow of treatment liquid and medicament is discharged through a releasably mounted appliance head or tip for use, by way of example, in cleaning the teeth and stimulating the gums of the user.

18 Claims, 5 Drawing Sheets

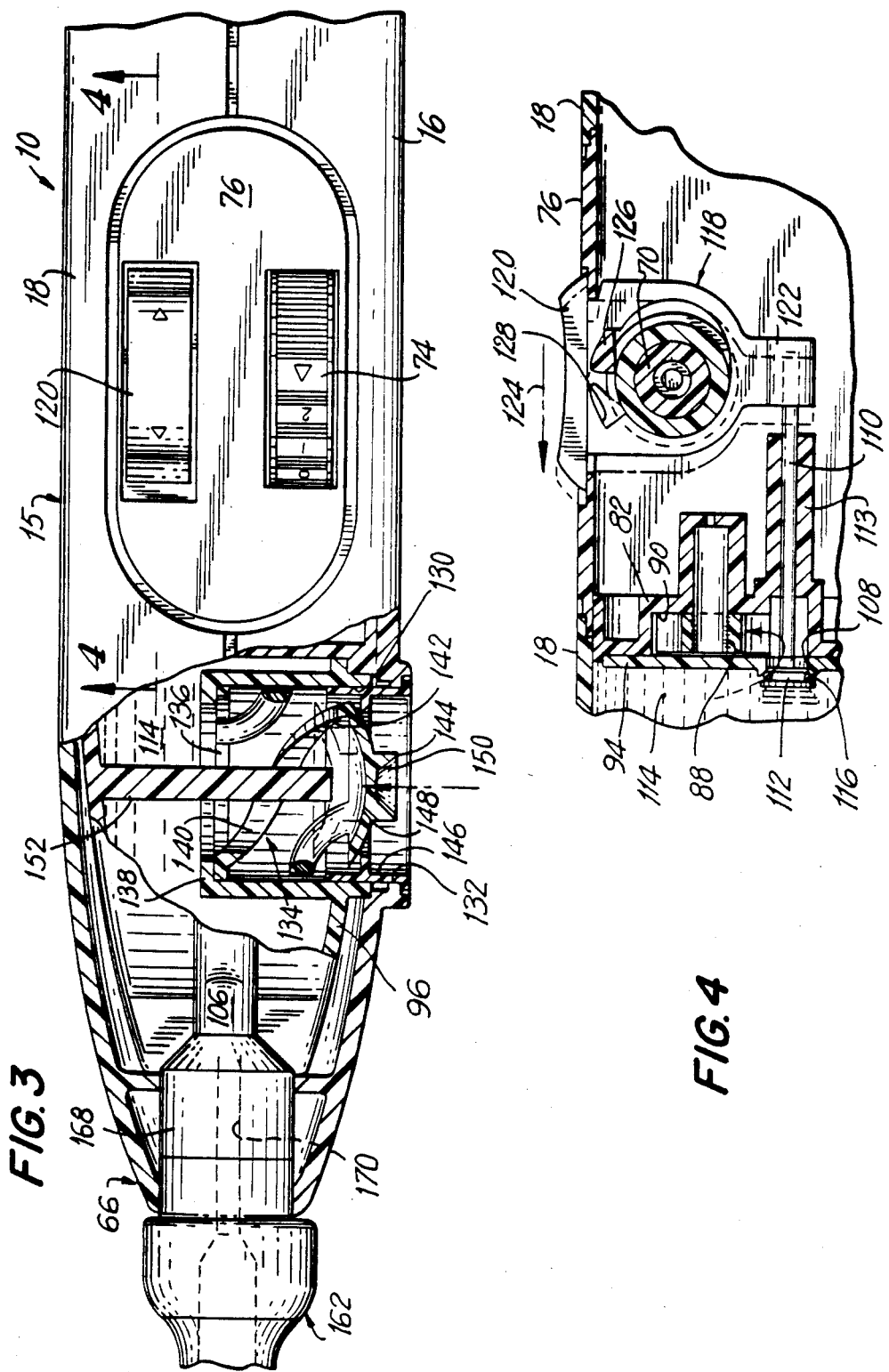

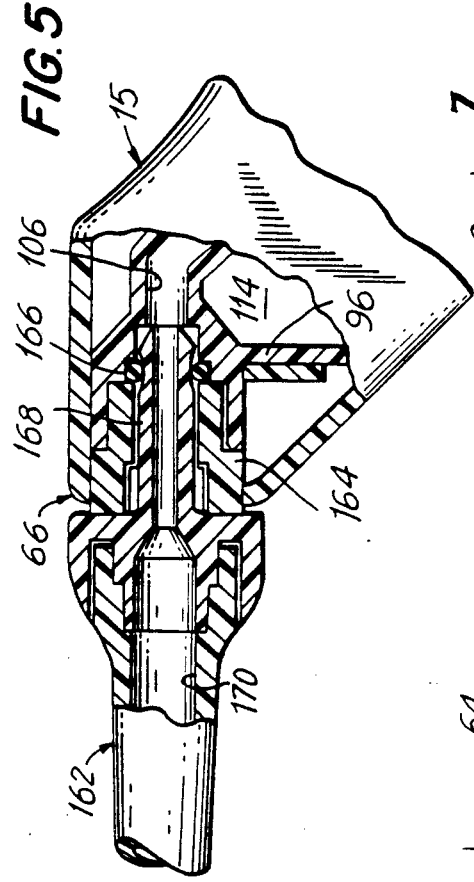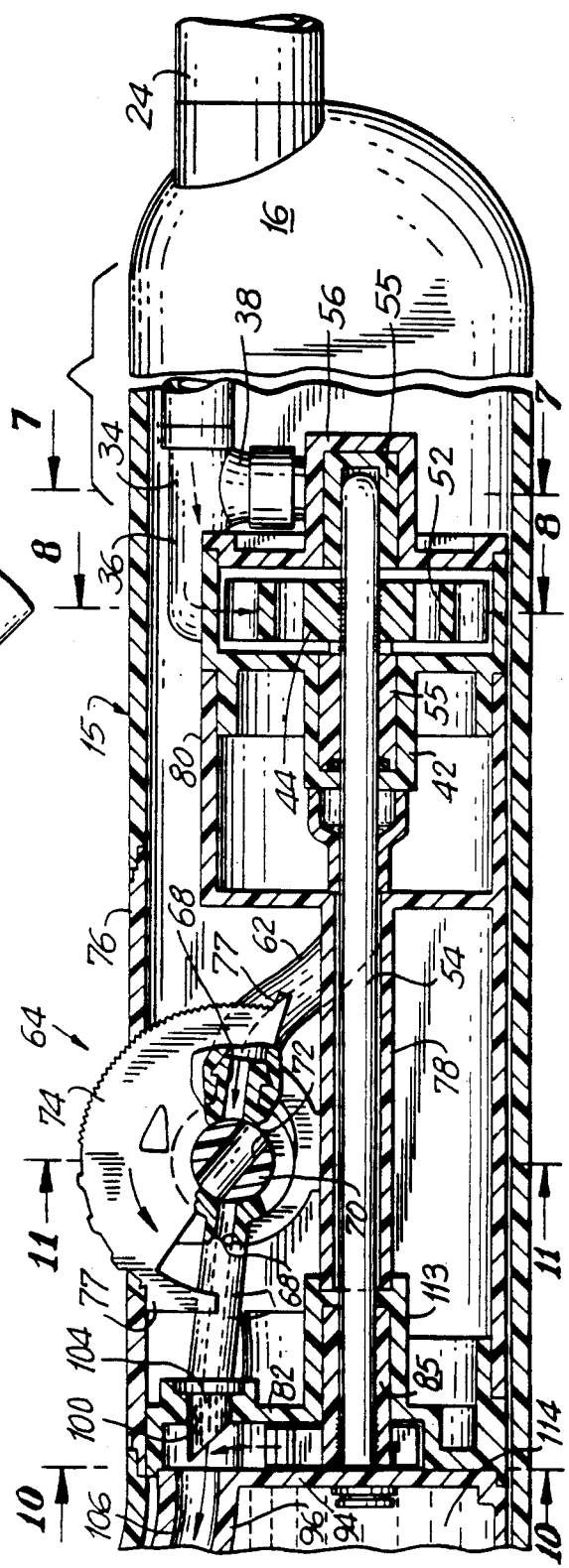

HAND-HELD ORAL IRRIGATING DEVICE

FIELD OF THE INVENTION

The present invention relates to devices for operatively producing and discharging a pulsatile stream of fluid, generally liquid. It is more particularly directed to such a device which is adapted for use in oral irrigation to cleanse the teeth and stimulate the gums of the user.

BACKGROUND OF THE INVENTION

Powered devices operable for producing a pulsatile stream of liquid for use in oral irrigation have long been known and are currently available commercially. Many such devices incorporate a refillable tank for receiving the treatment liquid—typically water—and require an electric current for developing a pulsating pressure used to deliver a water stream to an outlet tip or the like. Because spillage and dripping of the delivered liquid are common during their operation, these oral irrigators are most commonly used in the bathroom, proximate sinks and bathtubs and other supplies of running water, raising the distinct possibility of serious injury through shock or electrocution should the electrically-operated device inadvertently become submersed in water or develop an electrical short circuit.

Other such devices seek to overcome this drawback by providing non-electrical operating power. For example, U.S. Pat. No. 4,564,005 to Marchand et al. discloses an oral irrigating device designed for use in a bathtub or shower stall and operated solely by the incoming stream of continuous flow (i.e. nonpulsatile) water. The Marchand device includes a housing connected between the water supply pipe and the shower head, wherein the water stream is split into one branch that continues on to the shower head and a second branch that powers a turbine disposed in the housing. This second branch is again split into a first channel that is directed into turbine rotating contact with the turbine periphery and a second channel which is fed into interruptive communication with an off-axis aperture in the turbine disk to generate a pulsatile flow of the water from the continuous flow stream. The pulsatile flow is then directed, through an elongated conduit, to a hand-held tip for user-controlled direction of the pulsating output flow onto the teeth and gums. The hand-held tip also includes an optional open-mesh cage therewith for holding a tablet-form dentifrice or cleanser or other additive which, as the pulsating stream flows through the tip, melts and thereby mixes with the pulsatile stream for discharge from the tip.

Although the Marchand device is advantageously powered solely from the incoming continuous flow water stream, it suffers from several drawbacks that reduce its commercial desireability. For example, the operating components, such as the turbine, of the unit are contained in an elongated housing that is mounted physically between the water supply pipe and the shower head. The fact that this housing incorporates these components significantly increases its size and thereby substantially displaces the shower head from its originally-intended position over the bathtub or within the shower stall, a change which not all such installations are capable of practically or conveniently accommodating. In addition, undiscovered crimping or other blockage of the conduit connecting the housing to the hand-held discharge tip could quickly damage the unit's internal operating components located in the housing, such as the turbine, during operation or attempted operation of the device. Furthermore, in the event that it does become necessary to effect repairs to the turbine or other operating elements of the Marchand device, both the housing and the attached shower head must be removed from and then replaced on the water supply pipe since all of the unit's operating components are located in the housing. These procedures are extremely time consuming, potentially expensive should a professional plumber be required, and could easily result in leaks due to improperly-prepared or sealed connections when the various plumbing elements are rejoined both while the unit is being repaired and, again, when it must be reinstalled.

Another drawback lies in the manner in which the Marchand device provides for the mixing of an additive with the pulsatile water stream to be discharged from the hand-held tip. Such mixing occurs when the pulsatile stream causes melting of the solid-form additive and, as should be apparent, will result in inconsistent and virtually unpredicatable concentrations or ratios of additive to water. As a consequence, the effectiveness of the additive on the user's teeth and/or gums will be sharply reduced or, in some situations, almost entirely eliminated.

OBJECTS OF THE INVENTION

It is accordingly the desideratum of the present invention to provide a device for generating a pulsatile stream of treatment liquid while overcoming the various deficiencies and drawbacks of prior art devices.

It is a particular object of the invention to provide a liquid-powered hand-held oral irrigating device in which all operating components of the device are located in the hand-held housing.

It is another object of the invention to provide such a device in which an additive is controlledly mixable with the pulsatile discharge stream of liquid.

It is a further object of the invention to provide such a device in which the mixing of additive is effected by a pumping device operable for maintaining a predetermined and substantially consistent mixture ratio of additive to treatment liquid.

Yet another object of the invention is to provide such a device in which the additive pumping device is operated in conjunction with the pulse-generator.

A still further object of the invention is provide such a device in which the volumetric amount of additive mixed with the pulsed treatment liquid is dynamically adjusted in accordance with the volumetric flow of liquid through the pulse-generator.

Another object of the invention is to provide such a device incorporating operating components that are readily repairable without fully disconnecting the device from the treatment liquid supply.

An additional object of the invention is provide such a device that is relatively low in cost and which may be readily and economically manufactured utilizing well-known techniques.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein similar reference characters denote similar elements throughout the several views:

FIG. 3 is a sectional side view, partially broken away, taken along the lines 3—3 in FIG. 1;

FIG. 4 is a sectional side view, partially broken away, taken along the lines 4—4 in FIG. 3;

FIG. 5 is a sectional side view, partially broken away, taken along the lines 5—5 in FIG. 1;

FIG. 6 is a sectional side view, partially broken away, taken along the lines 6—6 in FIG. 1;

DETAILED DESCRIPTION OF THE PREFERRED EMBODIMENT

The present invention is directed to an oral irrigating device which, when used in conjunction with an input stream of continuous flow treatment liquid, outputs a pulsating flow of the liquid. As used herein, the term "continuous flow" is intended to distinguish a flow of liquid at a substantially constant—or at least a slowly or inconsistently varying—volumetric rate from the pulsatile flow produced by and output from the device of the present invention. Moreover, it is generally contemplated, particularly with respect to the primary intended utility of the inventive embodiment herein disclosed, that the treatment liquid will comprise water, and the following description will therefore most often expressly refer to that liquid as water. It should, however, be understood that no limitation on the scope of the present invention is intended by such references, and that the treatment liquid used in conjunction with the inventive device may accordingly comprise any liquid deemed suitable by and at the option of the user.

In any event, the inventive irrigating device is particularly noteworthy in that, other than its connection to the incoming continuous flow treatment liquid stream, it is entirely self-contained within a conveniently hand-held applicator housing and, in addition, is powered solely by the incoming liquid stream so as to require no external or otherwise stored source(s) of energy. Moreover, the irrigating device of the invention is constructed so that, at the option of the user, a highly concentrated medicament or additive stored in the applicator housing may be automatically mixed, at a predetermined and substantially constant volumetric rate and ratio, with the pulsating liquid stream generated from the incoming flow to define a pulsating flow of medicated treatment liquid for discharge from the device.

Figure 1:
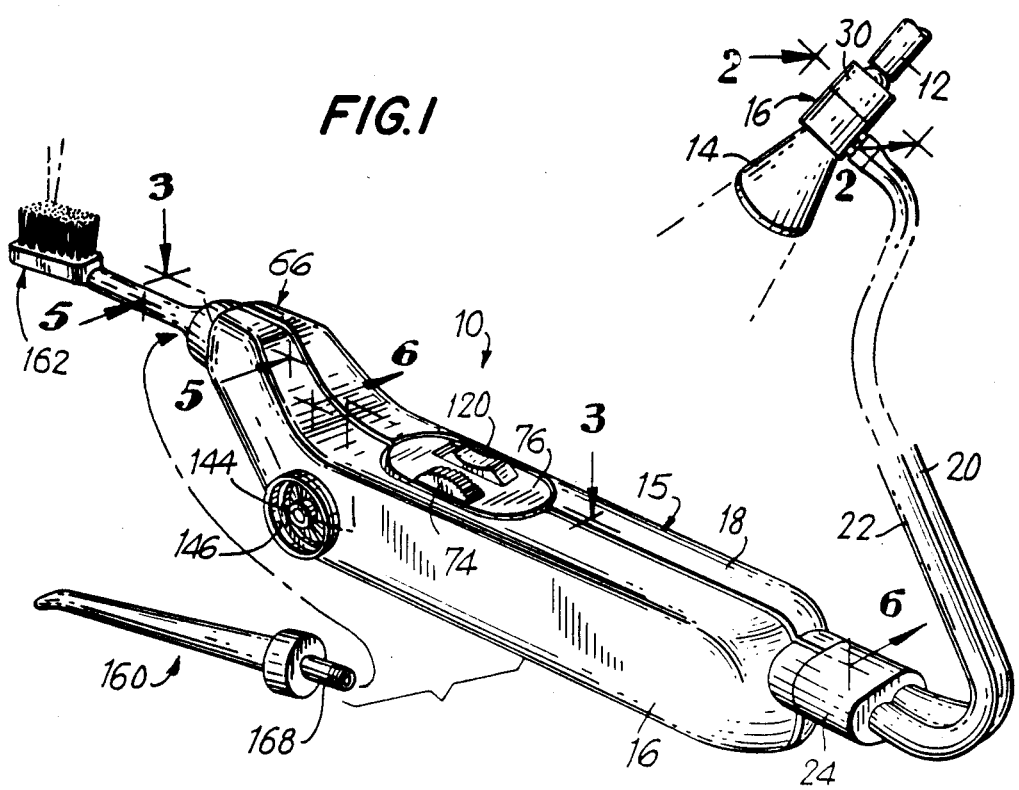
FIG. 1 is an elevated perspective view of a hand-held oral irrigating device constructed in accordance with the present invention and depicted in operative association with a conventional shower head.
Figure 2:
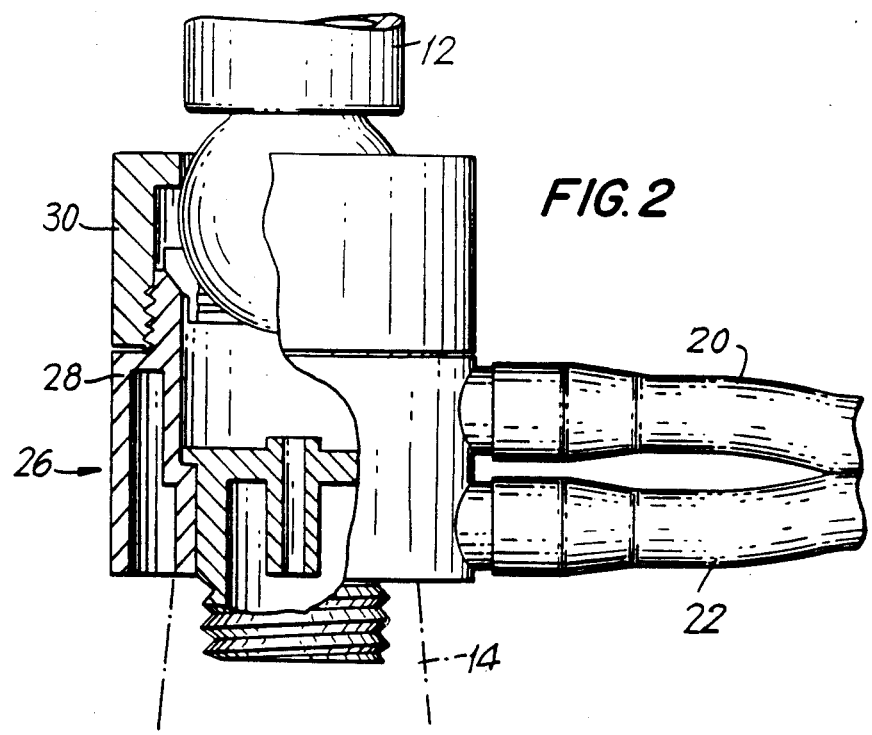
FIG. 2 is a sectional side view, partially broken away, taken along the lines 2—2 in FIG. 1.

Turning now to the drawings, which illustrate a currently preferred embodiment of the invention, the hand-held oral irrigating device or applicator 10 is shown in FIG. 1 in a typical implementation connected to a conventional water supply line 12 for an attached shower head 14. The applicator housing or body 15 is preferably configured and contoured to maximize its ability to be comfortably and conveniently hand-held during periods of use and operatively carries, at or proximate its forward or distal end, a releasably and interchangeably retained appliance heads such, for example, as the representatively shown elongated irrigating tip 160 and toothbrush 162.

The applicator housing 15 is principally formed by interengaging first and second shell halves or parts 16, 18 and the unit's internal operating components communicate with the supply line 12 through a pair of flexible delivery and return conduits 20, 22, respectively. Each of the conduits 20, 22 is connected at its opposite ends to the applicator 10 through a rear end-mounted strain relief collar 24 and to the supply line 12 at an adapter 26 which is interposed between the line 12 and shower head 14. The adapter 26 may be constructed in any convenient manner, such for example as shown in FIG. 15 wherein it comprises a housing 28 that is threadedly secured to and between the usual supply line connector element 30 and the shower head 14. Within the interior of the adapter housing 28 the input stream of continuous flow treatment liquid—i.e. water in the disclosed embodiment—is split into a first portion that continues on to and for normal discharge through the shower head and a second portion that is directed into the flexible delivery conduit 20 for transmission to the hand-held applicator 10. A user-operable valve (not shown) of any suitable form may also be incorporated in the adapter housing 28 to enable selective on-off or variable control of the flow of water to the applicator 10 through the conduit 20 through user manipulation of an associated valve control handle or actuator or the like.

Figure 8:
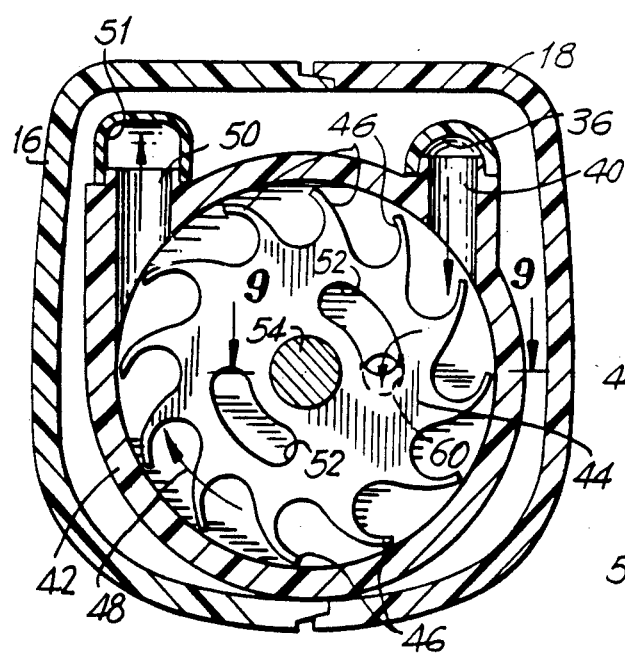
FIG. 8 is a cross-sectional view taken along the lines 8—8 in FIG. 6.

The continuous flow stream of water directed through delivery conduit 20 from supply line 12 is fed to a primary inlet tube 34 (FIG. 6) which splits the incoming flow into first and second channels 36, 38. The first channel 36 feeds an inlet port 40 of an internal housing 42 within which a turbine or impeller 44 is operatively mounted for rotation about its central axis. The turbine is provided with a multiplicity of wings 46 carried about its periphery and suitably curved or configured so that the continuous flow water stream directed onto the wings through the inlet port 40 effects rotation of the turbine in the direction of the arrow 48 in FIG. 8. An outlet port 50 on the turbine housing 42 is connected, by a linking tube 51, to the flexible return conduit 22 for returning the continuous flow water entering the housing 42 through inlet port 40 to the adapter 26 and shower head 14 for discharge from the head after its turbine-rotating passage through the housing 42. A plurality of apertures 52 are also defined in and through the central disk of the turbine 44 in radially offset relation to the turbine axis. These apertures may, as illustrated in FIG. 8, be elongated in the circumferential direction of the turbine disc. An elongated shaft 54 is tightly journalled axially through or otherwise secured to the turbine so that the shaft 52 rotates with the water-driven turbine 44. Bushings 55 may be provided in the turbine chamber—i.e. in the turbine housing 42 and the turbine housing cover 56—for rotatively supporting the rearward end of the shaft 52 on opposite sides of the turbine.

Figure 7:
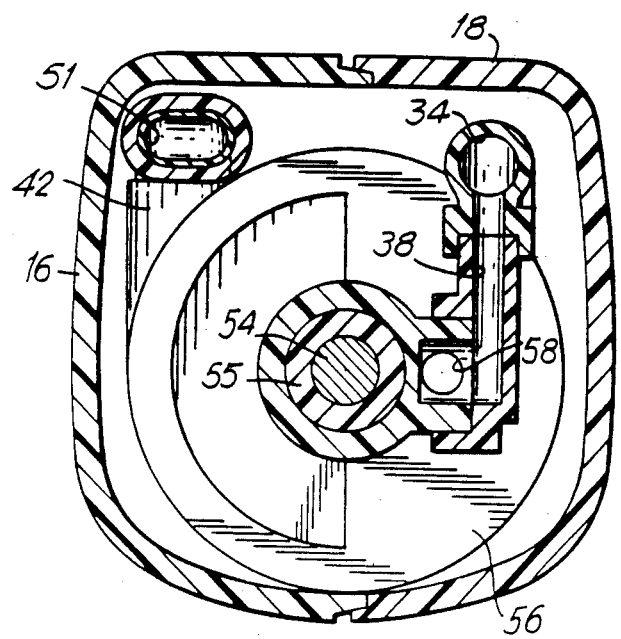
FIG. 7 is a cross-sectional view taken along the lines 7—7 in FIG. 6.
Figure 9:
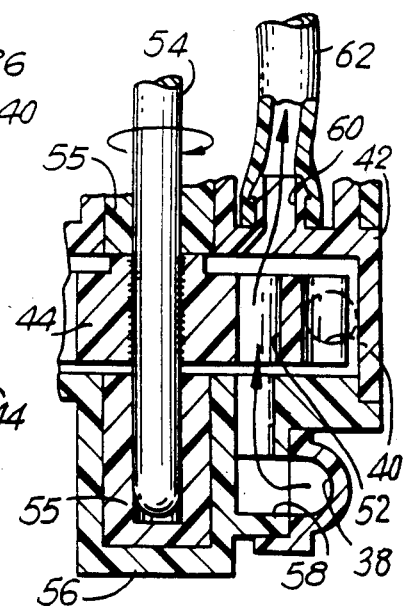
FIG. 9 is a sectional plan view, partially broken away, taken along the lines 9—9 in FIG. 8.

The turbine housing 42 is liquid-tightly closed by a cap or cover member 56 in which a pulse channel inlet port 58 connected to the second channel 38 is defined at an off-axis location aligned with the axial offset of the turbine apertures 52. A pulse channel outlet 60, similarly aligned with the turbine apertures offset, is provided in the turbine housing 42. Thus, and as best seen in FIGS. 7 to 9, the continuous flow stream of water entering the pulse channel inlet port 58 from the second channel branch 38 of primary inlet tube 34 is directed interruptedly against the turbine disk wall substantially transverse to its rotational plane at the offset location of the apertures 52. As the turbine operatively rotates, the apertures 52 are successively carried into registry with the port 58 and, thereby, into periodically and repetitively aligned registration with the continuous flow stream of water from port 58, thereby generating a pulsating flow of water that passes through the turbine apertures 52 and issues from the correspondingly aligned turbine housing outlet 60 into a distribution tube 62.

Figure 11:
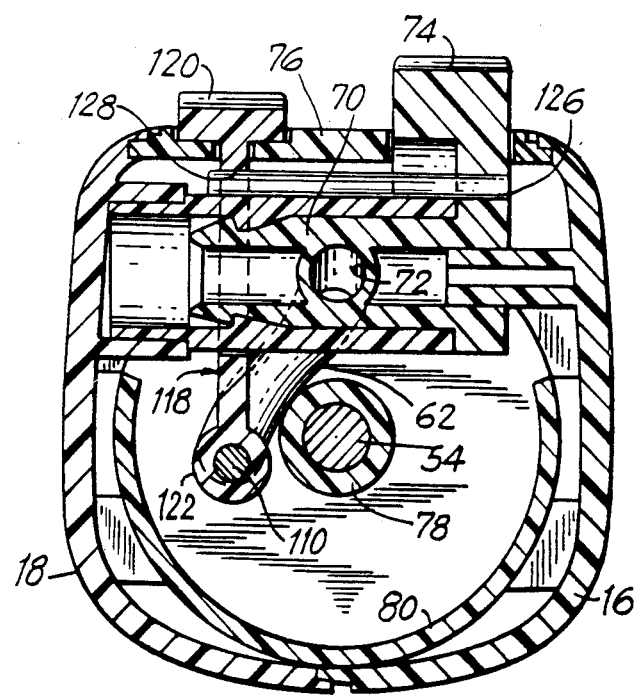
FIG. 11 is a cross-sectional view taken along the lines 11—11 in FIG. 6.

The forward or distal end of distribution tube 62, remote from its connection to the turbine housing outlet 60, is connected to a user-controllable regulator valve assembly 64 (FIGS. 6 and 11). This assembly 64 is user-operable for selectively adjusting the volumetric flow of pulsed treatment liquid emanating from the turbine housing 42 and directed, as hereinafter described, to the outlet 66 of the applicator housing 15. The valve assembly 64, which may in practice take on any functionally appropriate form, is disclosed herein by way of example as comprising a fixed passageway 68 that is interrupted by a cross-sectionally circular stem or elongated member 70 arranged for rotation about an axis transverse to the passageway 68 and having a bore 72 defined diametrically through the stem. Rotation of the stem 70 causes the bore 72 to be carried between opposed orientational extremes in which it totally blocks and fully opens, respectively, the passageway 68. For this purpose a user-rotatable knob 74 is carried dependingly on one end of the elongated stem 70 and projects upwardly through an inset face plate 76 of the applicator housing 15 for ready access by the user. Thus, selective user-effected rotation of the knob 74 carries the stem 70 and its bore 72 through a corresponding rotation by which the relative volumetric outflow of pulsed treatement liquid is varied between and including conditions of minimum and maximum flow. The valve assembly 64 is preferably constructed so that the pulsating stream of water from the turbine 44 is adjustable between fully unimpeded communication, on the one hand, and entirely blocked flow (as shown in FIG. 6), on the other, therethrough. Conditions of partial or reduced volumetric through-flow may thus be selected by the user in accordance with the desired pulsed output volumetric flow rate. If desired, the knob 74 may be knurled or have an otherwise suitably treated surface portion to facilitate user adjustment of its rotative position and may also carry indicia representing, for various rotative orientations of the knob, the relative pulsed liquid volumetric throughput of the valve assembly in the corresponding orientations. Stops 77 may also be provided as substantially radial extensions on the knob 74 for cooperative abutment with the face plate 76 to limit the permissable range of rotative adjustability of the knob.

Figure 10:
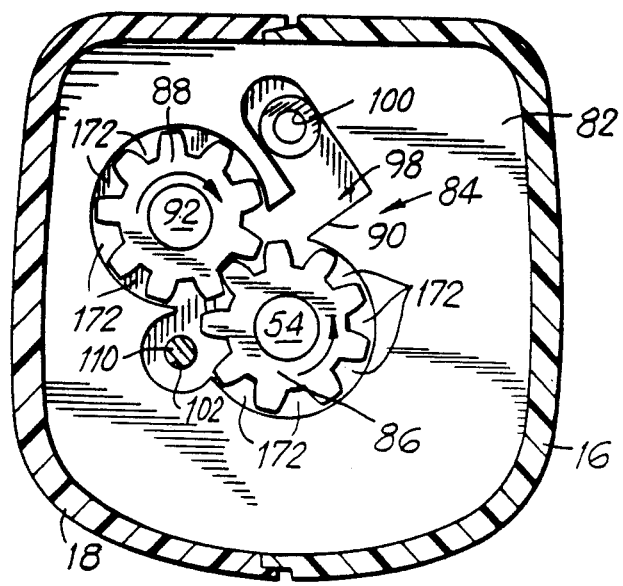
FIG. 10 is a cross-sectional view taken along the lines 10—10 in FIG. 6.

From its securement to the turbine 44 proximate the rearward end of the applicator housing 15, the shaft 54 extends forwardly through the elongated guide tube 78 of an intermediate sleeve element 80 and terminates within an internal housing 82 of a positive displacement gear pump 84 (FIG. 10). Here, again, a bushing 85 may be provided in the pump housing 82 to rotatably support the forward end of the turbine shaft 54. A driven gear 86 of the pump 84 is secured to the shaft 54 at or proximate its end remote from the turbine 44 so that, as the shaft is rotated by and with the water-driven turbine, it correspondingly drives or rotates the gear 86. An idler or freewheeling pump gear 88 is mounted in immediately adjacent relation to the driving gear 86 with the teeth of the two gears 86, 88 coupled in meshed engagement whereby rotation of the driven gear 86 effects corresponding rotation of the idler gear 88. The gears 86, 88 are disposed in a recess 90 in the wall of the pump housing 82, with the idler gear supported freely rotatably on a shaft 92 that projects from the pump housing wall into the recess 90. As should be apparent, the recess 90 defines, in conjunction with the end wall 94 of a medicament housing 96 that is mounted in the applicator body 15 immediately forward of and in abutment with the pump housing 82, a substantially closed pump chamber 98. Also located within the bounds of the recess 90 are two apertures 100, 102 through the gear pump housing 82 at opposite sides—i.e. upstream and downstream, or at the outlet and inlet sides, respectively—of the gear pump 84, as will hereinafter become clear. The first aperture 100 communicates with an extension 104 (FIG. 6) of the fixed passageway 68 of valve assembly 64 and is substantially aligned for fluid-directing communication with the rearward or proximal end of an outlet conduit 106 carried on the medicament housing 96 (FIG. 6). Outlet conduit 106, in turn, proceeds forwardly to the applicator housing outlet 66 (FIG. 5). Thus, pulsed treatment liquid issuing from the outlet port 60 of turbine housing 42 and passing through the valve assembly 64 is directed through the gear pump aperture 100 and into the outlet conduit 106 which feeds the pulsed liquid to housing outlet 66.

The second aperture 102 in the gear pump housing 82 is located in aligned registry with a feed opening 108 presented in the adjacently-disposed end wall 94 of the medicament housing 96. The aperture 102 is sized for snugly, but relatively slidably, receiving a longitudinally movable shaft 110 (FIG. 4) which extends through the feed opening 108 and carries, at its forward or distal end, a stopper or plug element 112. In a preferred form of the invention the portion 113 of the pump housing 82 through which the aperture 102 extends is sufficiently elongated so that the shaft 110 is disposed guidedly therein for much of its length. This elongation of the pump housing and aperture 102, in conjunction with suitable shaft seals (not shown), also facilitates the maintenance of a substantially liquid-tight fit between the shaft 110 and the interior periphery of the aperture. The stopper 112 is located within the medicament reservior-defining interior of the medicament housing 96 and is dimensioned so that, when disposed in abutment with the wall 94, the stopper fully covers and closes the feed opening 108 and thereby liquid-tightly seals the medicament-containing reservoir. To facilitate this liquid-tight closure of the feed opening 108 the stopper 112 may carry a circumferential O-ring 116 or the like, and/or the feed opening 108 may optionally be provided with an annular lip (not shown) to enhance the integrity of the seat against which the stopper is securely pressed for preventing, in this contact position of the stopper 112, unintended medicament loss or outflow from the reservoir 114 through the feed opening 108.

The stopper is also movable, to the left and from the solid (i.e. contact) to the broken lines position in FIG. 4, into sufficiently spaced apart relation to the medicament tank end wall 94 to permit the dispensing of stored medicament from the reservoir 114 into the gear pump chamber 98 through feed opening 108. For this purpose, a switch member 118 is mounted for sliding movement axially along the elongated applicator housing 15. Switch member 118 includes an exteriorly-located, finger-engageable slide 120 projecting through the inset face plate 76 for ready user access and an internally-disposed socket or carrier 122 to which the rearward end of the stopper shaft 110 is secured. This arrangement enables the user to selectively open or close the medicament feed opening 108 through finger-driven manipulation of the slide 120 in or against, respectively, the direction of the arrow 124 in FIG. 4.

The operation of the gear pump 84 should now be apparent. Turbine-driven rotation of the shaft 54 causes rotation of the coupled gears 86, 88 in the respectively counterclockwise and clockwise directions indicated in FIG. 10. With the stopper 112 retracted or spaced from end wall 94 so as to open the medicament feed opening 108, stored medicament from reservoir 114 enters the bottom (in FIG. 10) of the pump chamber 98. The medicament is then carried upwardly by the rotation of each gear 86, 88—in the interstices 172 between adjacently-disposed teeth on each gear—about the circular peripheries of the gear-containing portions of the recess 90. Those skilled in the art will recognize that the gear pump 84 creates a higher pressure at its outlet side, relative to its inlet side, by reason of the pumped movement of liquid from the storage reservior-fed inlet to the outlet of the pump. Medicament so pumped to the top (in FIG. 10) of pump chamber 98 there meets and mixes with the pulsed stream of water (i.e. treatment liquid) from valve assembly 64 that enters the pump chamber through aperture 100 and exits the chamber through outlet conduit 106. Thus, the pulsating liquid fed through outlet conduit 106 to applicator outlet 66 and the attached appliance head—such as the toothbrush 162 or irrigating tip 160, for example—is, with the feed opening 108 open, a mixture of the pulsating treatment liquid generated by the turbine 44 and the stored medicament from the reservoir 114. This mixture is referred to herein as medicated treatment liquid.

A particularly noteworthy and important feature of the inventive applicator device lies in its ability to maintain a substantially constant volumetric ratio of the amount of stored medicament that is mixed with the pulsed treatment liquid. Because the gear pump 84 is directly operated by the turbine 44, the rate at which the pump transfers medicament from the storage reservoir 114 into the pulsed treatment liquid stream is constantly and dynamically varied in accordance with the pulsed stream flow rate. Put another way, the turbine rotates at a rate substantially determined by the pressure or volumetric flow rate of the incoming continuous flow liquid received through the delivery conduit 20. In general, the faster the turbine rotates, the greater the volumetric flow of pulsed treatment liquid issuing from the turbine housing outlet 60. Rotation of the turbine 44 correspondingly rotates the shaft 54 at the same rate. Likewise, the shaft 54 correspondingly rotates the pump's driven gear 86, which in turn rotates the pump's idler gear 88, at the same rate. And the faster the gears 86, 88 rotate, the greater the volume per unit time of liquid medicament that the gear pump transfers from its inlet adjacent the reservoir feed opening 108 to its outlet for mixture with the pulsating flow of treatment liquid. Accordingly, variations or changes in the volumetric flow rate of pulsating treatment liquid issuing from the turbine housing outlet 60 are correspondingly reflected in the relative volumetric rate at which stored medicament is pumped into and mixed with the pulsating stream at the pump outlet side. This commonly-driven or coupled arrangement of the pulse-generating turbine 44 and gear pump 84 advantageously serves to maintain a substantially constant, predetermined ratio in the volumetric flow of medicament to pulsed treatment liquid fed to the selected appliance head through the outlet conduit 106. One benefit derived from this result is the ability to predeterminately control the dilution of stored medicament and thereby assure its effectiveness for the contemplated use.

The knob 74 of the flow control valve assembly 64 carries, from a point radially-inwardly spaced from its periphery, an elongated interlock bar 126 for cooperative engagement with switch member 118. More particularly, as seen in FIGS. 4 and 11 the bar 126 extends substantially perpendicular or otherwise transverse to the plane of knob 74 and into the confines of a predeterminately shaped or keyed cutout 128 defined in that portion of the switch member 118 which joins slide 120 and shaft carrier 122. Thus, as the knob 74 is rotated by the user to selectively vary the volumetric flow of pulsating water between unimpeded and fully arrested flow conditions, the bar is shifted laterally to its elongation between the broken and solid line orientations, respectively, depicted in FIG. 4. With continued reference to FIG. 4, the cutout 128 is configured so that when the knob is rotated to fully arrest or cut off the flow of pulsating water through valve assembly 64—i.e. to its maximum permitted clockwise rotation in the figure—the bar 126 engagedly abuts the rearward (i.e. rightward) edge of the cutout and thereby prevents movement of the slide 120 (and, correspondingly, of shaft carrier 122) from the solid to the broken line positions in FIG. 4. Put another way, by virtue of the cooperative provision of the interlock bar 126 and shaped cutout 128, the stopper 112 is maintained and prevented from being displaced out of its sealing engagement with the medicament reservoir feed opening 108.

Referring now to FIG. 3, the medicament housing 96 is also provided with a fill opening 130 and the applicator shell part 16 with an access opening 132 aligned with the fill opening 126. A spring element 134 includes a ring-shaped base 136 that is supported on a seat 138 defined in the medicament reservoir 114. The spring element 134 is constructed as a plurality of helical coil legs 140 which connect the base 136 with an oppositely and relatively outwardly-disposed head 142 of concavo-convex or conical shape and carrying a central upstanding boss or button 144. The spring legs 140 urge the head 142 outwardly—i.e. in the direction of the openings 130, 132—and, in order to capture the spring within the medicament housing 96, a retainer element 146 is secured to the shell part 16. The retainer 146 is dimensioned to tightly abut, and thereby liquid-tightly close, the fill opening 130 and is further provided with a central aperture 148 dimensioned smaller than spring head 134 and at least slightly larger than boss 136 which, as seen in the drawing, projects outwardly through aperture 148. The lip or rim of aperture 148, which serves as a valve seat, is preferably tapered or otherwise shaped so as to match the contour of the spring head 142 and thereby facilitate maintainance of the desired liquid-tight engagement therebetween.

As should now be apparent, the outwardly-directed urgency of the expansion spring element 134 drives and normally maintains its head 142 into and against the retainer 146 whereby the aperture 148 is sufficiently liquid-tightly closed as to prevent the leakage of medicament therethrough. Thus, the only normal access to medicament stored in the reservoir 114 is through the feed opening 94 in housing end wall 94. Nonetheless, when it is desired to fill or refill or otherwise add medicament to the reservoir 114, the boss 144—which projects and is thus readily accessible through the retainer aperture 148—is pressed inwardly to provide a sufficient clearance between the spring head 142 and the lip of aperture 148 for the passage or flow of medicament. For this purpose and to facilitate such a refill operations, medicament may be supplied in a bottle or container (not shown) which includes a dispensing head configured to mate with the boss 144 and thereby facilitate the addition of medicament into the reservoir 114. For example, the dispensing head of the container may incorporate a tapered projection receivable in a depression or concavity 150 in the projecting spring head boss 144. An inwardly-projecting post 152 may also be provided on the medicament housing 96 to limit the inward travel of the spring head 134 during refilling of the reservoir with medicament.

The preferably releasably securement of a selected head appliance—such as the toothbrush 162—may be implemented by any appropriate structure suitable for effecting a substantially liquid-tight connection between the applicance and the housing outlet 66 at the forward or head end of the applicator body 15. For example, as shown in FIGS. 1 and 5 the head end of the applicator may be provided with a gasket or bushing 164 and an internal rib or projection 166 for snap-fit and substantially liquid-tight receipt of a grooved finger-like adapter 168 integrally carried at the rearward end of the toothbrush 162 or tapered irrigating tip 160 or other appliance for use with the device 10. Each appliance head will also have a passage 170 defined therewithin and extending from its adapter 168 to or proximate its distal or work end for communicating pulsed liquid from the applicator outlet 66—more particularly the outlet conduit 106—to the work end of the appliance.

In use, the inventive applicator 10 is connected to a source of continuous flow treatment liquid, such as the water supply line 12 for shower head 14, by threaded securement of the adapter 26 between the line 12 and head 14. A first portion of the incoming continuous flow water stream from delivery conduit 20 and entering the turbine housing 42 at inlet port 40 is directed onto the turbine wings 46 whereby the turbine 44 is rotated at a rate related to the incoming stream volumetric flow. The turbine-rotating stream exits the housing 42 at outlet port 50 and is returned to the adapter 26 and shower head 14 through return conduit 22.

A second portion of the incoming continuous flow water stream from delivery conduit 20 enters the turbine housing through inlet port 58 on cover 56 and is directed into interruptive engagement with the turbine disk. More particularly, this second water stream is directed for periodic passage through the apertures 52 which are successively moved into and out of registry with the port 58 as the turbine rotates. The resulting pulsating flow of water exiting the turbine apertures 52 moves through pulse channel outlet port 60 of turbine housing 42 and is fed, by distribution tube 62, to flow control valve assembly 64. Assembly 64 is selectively and optionally adjustable by the user to vary the volumetric flow of pulsed liquid fed to and through an appliance head mounted or secured to the applicator housing 15.

With the slide 120 fully rearwardly retracted—i.e. to the right in the drawings—the stopper 112 closes the reservoir feed opening 108 so as to prevent the flow of stored medicament from the reservoir 114 into the gear pump chamber 98. In this condition, although the gears 86, 88 continue to operatively rotate under the driving rotation of the turbine shaft 54, no stored medicament reaches the pump chamber and none is accordingly fed from the inlet to the outlet side of the pump. Accordingly, the pulsed stream of water from the valve assembly 64 proceeds unmodified into and through the outlet side of the pump chamber and thence into the outlet conduit 106 and the mounted appliance head such, for example, as the irrigating tip 160 or toothbrush 162.

When, on the other hand, the slide 120 is forwardly shifted—i.e. to the left in the drawings—the stopper 112 is driven out of abutment with and into spaced relation to the medicament chamber end wall 96 whereby the feed opening 108 is sufficiently opened to permit stored medicament from the reservoir 114 to enter the gear pump chamber 98. In this condition, medicament exiting the reservoir through opening 108 is pumped by the coupled rotating gears 86, 88 to the pump outlet side at which it automatically mixes with the pulsating stream of water fed to the pump chamber from the valve assembly 64. The resulting combined pulsatile stream of medicated treatment liquid exits the pump chamber 98 through outlet conduit 106 and, as before, is thereby directed to the mounted or attached appliance head.

The operating advantages provided by the cooperating interlock bar 126 and keyed cutout 128 should now be apparent. Since the turbine 44 is continuously rotated by the first portion of the incoming continuous flow stream of water whenever the delivery conduit is connected to an active (i.e. running) flow of water, the pump gears 86, 88 are also continuously rotated at such times. Accordingly, whenever the slide 120 is forwardly displaced so as to open the reservoir feed opening 108, medicament stored in the reservoir 114 will be pumped through the gear pump 84 to the outlet conduit 106 for discharge from the mounted appliance head. Such pumping of the medicament would normally occur even when the valve assembly 64 is operatively adjusted by the user to fully arrest or cut off the flow of pulsating water into the pump outlet side, thereby resulting in, inter alia, unintended and undesireable waste of stored medicament. The interlock bar 126 and keyed cutout 128 cooperate to avoid such waste or loss of medicament by preventing unsealing of the reservoir feed opening 108 whenever the valve assembly 64 has been adjusted so as to fully arrest the flow of pulsating water therethrough. Thus, the applicator 10 is operable to cut off the flow of all liquids to and through a mounted appliance head during periods of nonuse, thereby enabling the inventive device to be permanently or semi-permanently connected to the supply line 12. As previously noted, a user-operable valve (not shown) may optionally be provided in the adapter 26 for selectively arresting the flow of all incoming treatment liquid through the delivery conduit and thereby halting continued driven rotation of the turbine 44 and pump gears 86, 88 during periods in which the shower head 14 is in use but the device 10 is not.

The present invention, as herein disclosed, accordingly provides a substantially self-contained, self-powered device requiring only that it be connected to a source of continuous flow treatment liquid such, by way of example, as water. It converts the input stream of continuous flow liquid to a pulsatile flow and mixes a stored medicament with the pulsatile stream, finally discharging the pulsating combined flow of treatment liquid and medicament through a preferably releasably attached appliance head such as an irrigating tip or toothbrush. Both the mechanism for converting the input continuous flow stream to a pulsatile flow and the medicament mixing pump device are operated by the input liquid stream and, advantageously, the volumetric ratio of medicament to treatment liquid in the pulsatile output stream is maintained substantially constant irrespective of variations in the volumetric flow rate of treatment liquid delivered from its source to the inventive irrigation device.

As used herein, the term medicament is employed in a broad sense and is intended to include any and all flowable fluids which the user desires to mix or add to the treatment liquid for the contemplated use. Although it is generally contemplated that the medicament be in liquid form, modifications to the pump assembly for distributing into the pulsatile output stream a medicament in the form, for example, of a flowable solid may be readily made and are within the intended scope of the invention. In any event, where the device 10 is to be employed by way of example as an oral irrigating device for cleaning the teeth and stimulating the gums of the user—as in the embodiment depicted in the drawings—the medicament may comprise a mouthwash, or dentrifice, or cleanser, or plaque remover, or any other additive or combination of additives at the option and selection of the user. It should also be recognized and appreciated that the ability of the inventive device to maintain a substantially constant volumetric ratio of medicament to treatment liquid in the pulsatile output stream advantageously permits the use of medicaments stored in known concentrations or otherwise requiring, for effective use, particular dilution ratios or treatment amounts or the like. Thus, by way of illustration a medicament may be stored in the internal reservoir in a highly concentrated form which could not be comfortably or effectively directly ingested by a user, the construction and operation of the inventive device assuring that only an adequate and effective dilution of the concentrate will be discharged in a pulsatile stream through the mounted appliance head or tip.

While there have been shown and described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. An applicator for discharging a pulsating flow of a medicated treatment liquid, comprising:

a housing having an inlet for receiving a variable rate stream of continuous flow treatment liquid and an outlet for discharge of a pulsating flow of the treatment liquid;

a reservoir defined in said housing for containing a supply of liquid medicament;

means in said housing operable for pumping the liquid medicament out of said reservoir at a controllable volumetric rate; and dual function means in said housing for converting the input stream of continuous flow treatment liquid to a pulsating liquid flow and for operating said pumping means for dispensing the contained medicament into the pulsating flow of treatment liquid at a volumetric rate controlled by said dual function means in accordance with the variable rate inlet stream of continuous flow treatment liquid so as to mix the medicament with the pulsating treatment liquid at a substantially constant predetermined ratio and thereby define a combined pulsating flow of medicated treatment liquid for discharge through said housing outlet.

2. An applicator in accordance with claim 1, wherein said dual function means comprises a turbine mounted for rotation by the variable rate flow of continuous flow treatment liquid, and coupling means between said pumping means and said turbine for operating said pumping means at a rate controlled by the rotation of said turbine.

3. An applicator in accordance with claim 2, wherein said coupling means comprises a shaft rotatable with said turbine and operatively connected to said pumping means.

4. An applicator in accordance with claim 2, wherein said pumping means comprises a positive displacement gear pump.

5. An applicator in accordance with claim 4, wherein said reservoir includes an outlet, and said pump has an inlet in liquid communication with said reservoir outlet and an outlet in liquid communication with the pulsating liquid flow from said turbine.

6. An applicator in accordance with claim 5, further comprising user-switchable means for selectively opening and closing said reservoir outlet so as to enable and prevent, respectively, dispensing of the contained medicament from the reservoir for mixing with the pulsating treatment liquid.

7. An applicator in accordance with claim 2, wherein said pumping means comprises a positive displacement gear pump having a driven gear operatively rotated through said coupling means in accordance with the rotation of said turbine.

8. An applicator in accordance with claim 7, wherein said coupling means comprises a shaft rotatable with said turbine and operatively connected to said driven gear for rotating said gear.

9. An applicator in accordance with claim 2, wherein said turbine includes an aperture defined therethrough and said housing inlet comprises a first part for directing the continuous flow treatment liquid into turbine rotating engagement with said turbine and a second part for directing the continuous flow treatment liquid into repeatedly-interrupted fluid communication with said aperture to create said pulsating liquid flow as the continuous flow treatment liquid interruptedly passes through said aperture during rotation of said turbine.

10. An applicator in accordance with claim 1, further comprising user-adjustable valve means for selectively adjusting the volumetric flow rate of the pulsating liquid flow from said dual function means.

11. An applicator in accordance with claim 1, wherein said reservoir includes an inlet, and spring-loaded means at said reservoir inlet for normally liquid-tightly closing said reservoir inlet and displaceable against a spring urgency for enabling a flow of liquid into the reservoir through said reservoir inlet for selective addition of liquid medicament to said reservoir.

12. An applicator in accordance with claim 1, wherein said treatment liquid is water.

13. An applicator in accordance with claim 1, wherein said liquid medicament is a mouthwash and is stored in said reservoir in a concentrated form requiring substantial dilution for use.

14. An applicator in accordance with claim 13, wherein said predetermined ratio is approximately 1 part liquid medicament to 9 parts treatment liquid.

15. An applicator in accordance with claim 14, wherein said treatment liquid is water.

16. An applicator in accordance with claim 1, wherein said predetermined ratio is approximately 1 part liquid medicament to 9 parts treatment liquid.

17. An applicator in accordance with claim 16, wherein said treatment liquid is water.

18. An applicator in accordance with claim 1, wherein said dual function means comprises a turbine mounted for rotation by the variable rate flow of continuous flow treatment liquid, and coupling means between said pumping means and said turbine for operating said pumping means at a rate directly related to the rotation of said turbine.

* * * * *